United States Patent [19]

Thomas et al.

[11] 4,435,308
[45] Mar. 6, 1984

[54] COMPOSITIONS BASED ON ALUMINUM HYDROXYCHLORIDES

[75] Inventors: Maryvonne Thomas, Boulogne Billancourt; Jean Grosbois, L'Isle Adam, both of France

[73] Assignee: Rhone-Poulenc Industries, Paris, France

[21] Appl. No.: 913,853

[22] Filed: Jun. 8, 1978

Related U.S. Application Data

[63] Continuation of Ser. No. 709,178, Jul. 27, 1976, abandoned.

[30] Foreign Application Priority Data

Jul. 31, 1975 [FR] France ................................ 75 23926

[51] Int. Cl.³ .............................................. C02F 5/10
[52] U.S. Cl. ..................................... 252/181; 210/702
[58] Field of Search ............. 210/42 R, 702; 252/180, 252/181

[56] References Cited

U.S. PATENT DOCUMENTS 3,497,459  2/1970  Nakamura et al. ............... 210/42 R
3,544,476 12/1970  Aiba et al. ........................ 210/42 R
3,929,666 12/1975  Aiba et al. ........................ 210/42 R Primary Examiner—Thomas G. Wyse
Attorney, Agent, or Firm—Burns, Doane, Swecker & Mathis

[57] ABSTRACT

Aluminum hydroxychloride compositions characterized by the presence of $SO_4^{-2}$ anions and at least one anion of selected organic acids are disclosed, as well as their particular utility in the treatment of soft water.

4 Claims, No Drawings

COMPOSITIONS BASED ON ALUMINUM HYDROXYCHLORIDES

This is a continuation of application Ser. NO. 709,178, filed July 27, 1976 abandoned.

BACKGROUND OF THE INVENTION

1. Field of the Invention

The present invention relates broadly to aluminum hydroxychloride compositions characterized by the presence of both $SO_4^{-2}$ anions and anions of selected organic acids. The present invention also relates to the utility of such compounds in the treatment of soft water.

2. Description of the Prior Art

Treatment of water and aqueous effluent by various aluminum salts in conventional and has long been based on the ability of such compositions as aluminum sulfate and aluminum hydroxychlorides to effect coagulation and flocculation of impurities therein. The latter of these compositions is currently enjoying an increasingly more important position in the treatment of water and aqueous effluent due to an enhanced capacity for such coagulating and flocculating of impurities and has, thus, received vast commercial attention.

Moreover, respecting these aluminum hydroxychlorides, it is known that the addition of certain anions to the basic composition provides a synergic effect in the ability to coagulate and flocculate impurities. This is particularly true of the $SO_4^{-2}$ anion, while it has been also suggested that the anions of phosphoric and chromic acids as well as various carboxylic acids such as citric acid, oxalic acid and various sulfonic acids may also be employed to these ends.

Notwithstanding the general efficacy of such compounds and compositions, it has been determined by applicants that the results are highly unpredictable depending upon such considerations as the anions involved and the solution to be treated. Thus, it has been observed that, although the addition of $SO_4^{-2}$ anions to aluminum hydroxychlorides indeed increases their effectiveness in a majority of applications, the same does not apply to the addition, even in large quantities, of most of the other anions enumerated above. More particularly, in the special and more difficult case of treating soft water, it has been determined that none of the various anions give satisfactory results, while, surprisingly, the $SO_4^{-2}$ anion is totally ineffective.

Accordingly, the need exists to provide effective coagulating and flocculating agents, particularly based upon the aluminum hydroxychloride compounds, for the treatment of soft water.

SUMMARY OF THE INVENTION

In accordance with the deficiencies of the prior art, it is a major object of the present invention to provide compounds efficient in the treatment of soft water to remove impurities contained therein.

Yet another object of the present invention is to provide compounds for treating water below a hardness value of about 6°TH (French scale, 1°TH corresponding to 10 mg/l. of alkaline earth metals (chiefly Ca and Mg) expressed as Ca $CO_3$/l.).

Yet another object of the present invention is to provide such compounds having utility for the treatment of soft water, which compounds are based upon aluminum hydroxychlorides.

Another object of the present invention is to provide aluminum hydroxychloride compounds characterized by the presence of anions of both $SO_4^{-2}$ and selected organic acids useful for the treatment of soft water.

In accordance with the present invention, it has surprisingly been determined that certain aluminum hydroxychloride compositions, characterized by the presence of $SO_4^{-2}$ anions and at least one selected organic anion, are exceedingly effective in the treatment of soft water. The organic anion is selected from the group of those adapted to form anionic or non-charged complexes with aluminum in a neutral or non-acidic medium. The most preferred organic anion is, thus, selected from the group consisting of the citric and sulfosalicyclic acids, the anion of pyrocatechol 3,5-disulfonic acid, and that of chromotropic acid. These organic anions may be provided either from the acid, itself, or from some other compound, the most suitable being salts of ammonium or the alkali metals. The organic anion from these materials is added to the aluminum hydroxychloride compound to be present in a quantity of at least 0.01 M/gram-atom of aluminum, while the $SO_4^{-2}$ anion is preferably present in the range of from about 0.05 to about 0.3 M/gram-atom of aluminum. Advantageously, the anions may be added to a precursor solution of aluminum hydroxychloride at any stage of its preparation.

Aluminum hydroxychloride compounds possessing these anions have been determined to be exceedingly effective in the treatment of water and aqueous effluent, particularly the treatment of soft water. Yet further objects and advantages of the present invention will become apparent to the skilled artisan upon examination of the detailed description of the invention.

DETAILED DESCRIPTION OF THE INVENTION

The present invention broadly relates to the treatment of water and aqueous effluent, and more particularly soft water, with aluminum hydroxychloride compounds characterized by the presence of anions of both $SO_4^{-2}$ and at least one selected organic acid. The $SO_4^{-2}$ anion is present in a proportion within the range of from about 0.05 to about 0.3 M/gram-atom of aluminum, while the organic anion is present in a range of from about 0.01 to 0.1 M/gram-atom of aluminum. The organic anion is selected from those known to form anionic or non-charged complexes with aluminum in a neutral or non-acid medium and is, preferably, selected from the anions of citric and sulfosalicyclic acids, pyrocatechol 3,5-disulfonic acid, and chromotropic acid. The organic ions are preferably supplied either from the acid or a suitable compound thereof, the most suitable being salts of ammonium or of alkali metals.

While the action of the $SO_4^{-2}$ anions, as synergic with aluminum hydroxychlorides, is known in the treatment of water, the manner in which the organic anions influence the coagulation and flocculation of impurities in soft water, and the superior results manifested thereby, is not entirely understood. While it is not intended that the invention be bound by any theoretical explanation, it is postulated that these anions initiate hydrolysis of the aluminum salts in a relatively acidic medium, partially replacing the hydroxyl ions present in low concentrations in soft water. Alternatively, there may be a coagulation-initiation process attendent neutralization of cationic positions in the products of hydrolysis of the aluminum salts by the anionic positions of groups formed on those products by the organic anions added. Regardless of the actual mechanistic explanation, however, actual observation demonstrates a surprising and highly effective action of the modified aluminum hydroxychlorides of the present invention.

The compositions according to the present invention may be produced simply and by numerous methods. For example, the desired organic anions may be added to aluminum hydroxychlorides which have been previously prepared to have incorporated therein the $SO_4^{-2}$ anion. Particularly suitable processes to effectuate this production of $SO_4^{-2}$-containing hydroxychlorides are described in applicants' French Patent Application Ser. No. 75.21661, filed July 10, 1975, and entitled "A Process for the Preparation of Aluminum Hydroxychlorides", corresponding to U.S. patent application Ser. No. 703,231, filed July 7, 1976, incorporated herein by reference and relied upon. The disclosure in these applications describes various and alternate methods for preparation of aluminum hydroxychloride compositions possessing various anions in addition to the chloride component and in which the OH/Al ratio is within the range of from about 1.2:1 to 1.7:1, which is most preferred for purpose of the present invention.

For matters of convenience and expediency, it is desirable to add the organic ions to the hydroxychloride compositions prepared in accordance with the foregoing applications, i.e., compositions already having the $SO_4^{-2}$ constituent present therein and exhibiting the desired OH/Al ratio. It is likewise possible to add the desired anions to aluminum hydroxychlorides of lower basicity than those resulting from the above-identified method, such as those compounds obtained by the processes described in applicants' French Pat. No. 73.36846, filed Oct. 16, 1973, entitled "Aluminum Hydroxychlorides and Their Preparation Process", and the two additions No. 74.22201 and No. 74.22968, filed June 26, 1974 and July 2, 1974, respectively, all incorporated by reference and relied upon. Obviously, in cases where the anions are added to aluminum hydroxychlorides exhibiting a basicity too low for the application presently envisaged, the basicity of the compounds must be altered by partial neutralization as is described in the aforenoted French Patent Application No. 75.21661.

Through appropriate employment of the techniques described in the foregoing patents and patent applications, as well as exemplified below, and with the present discovery that certain additional organic anions will provide improved results in the treatment of soft water, it is possible to achieve a formulation of compositions based on aluminum hydroxychlorides by adding $SO_4^{-2}$ anions and the organic anion or anions independently or together, at any stage in the preparation of the hydroxychlorides. This clearly facilitates the adaptability of currently employed techniques to the preparation of the compounds in accordance with the present invention.

In order to further elucidate upon the objects and advantages of the present invention, the following examples will be given, the same intended to be illustrative and in no wise limitative. Prefacing this exemplification, however, it should be appreciated by the skilled artisan that the most appropriate hydroxychloride compounds are those which exhibit a basicity in the ultimate product, which may be defined as the OH/Al ratio of the products, of from about 1.2:1 to 1.7:1 as disclosed in the aforenoted French Patent Application No. 75.21661 and its United States counterpart.

EXAMPLE I 845 kg of Bayer hydrate of alumina, containing 58.5% of alumina, $Al_2O_3$, are gradually fed to a reactor containing 800 l. of 35% hydrochloric acid under agitation. As reaction kinetics slow, the reaction medium is heated under reflux for 6 hours. The solution is allowed to cool for 5 hours and is decanted, the clear liquid floating on the surface being siphoned off. Subsequently, the non-reacted portion from the foregoing reaction is then reached with 800 l. of hydrochloric acid and 420 kg of hydrate of alumina as above. Typically, such a method yields a solution of aluminum hydroxychlorides of crude formula:

$$AlOH_{1.05}Cl_{1.95}$$

containing 245 g/l. of alumina, $Al_2O_3$.

1 m³ of this non-basic solution is placed in a tank and agitated; then, 0.7 m³ of a 170 g/l. solution of sodium carbonate, Na $CO_3$, is slowly added over a period of about 1 hour and at ambient temperature, the speed at which the solution is introduced being controlled according to the loss of $CO_2$. 230 kg of coarsely ground sodium sulfate, $Na_2$ $SO_4$, are then added and the resultant mixture agitated for 3 hours. At that time, 40 kg of citric acid $C_6H_8O_7.H_2O$ are added. This yields a complex product in accordance with the present invention having the general formula:

$$AlOH_{1.48}Cl_{1.95}SO_{4\ 0.15}Na_{0.73}\text{citric acid}_{0.04}$$

EXAMPLE II

The process of Example I is repeated with the exception of the addition of the citric acid. Accordingly, the product obtained is not within the scope of the present invention.

EXAMPLE III

The process of Example I is again repeated with the exception of the addition of sodium sulfate. Thus, again, the product obtained is not in accordance with the present invention.

EXAMPLE IV

The process of Example I is again repeated with the exception that a greater quantity of citric acid is added, being equal to 0.15 M/gram-atom of aluminum. Accordingly, the product obtained thereby is not within the scope of the present invention.

EXAMPLE V 240 kg of aluminum chloride, $AlCl_3.6H_2O$ and 10 kg of 2-hydroxy 5-sulfobenzoic acid (sulfosalicyclic acid) are dissolved into 600 L. of water under agitation at a temperature approaching the boiling point of the solution. Subsequently, the solution is allowed to cool and, when its temperature approaches ambient, 126 kg of sodium bicarbonate, $NaHCO_3$, followed by 32 kg of sodium sulfate, $Na_2SO_4.10H_2O$, are gradually added over the course of about 1 hour while the solution is maintained under conditions of agitation. This yields a product according to the present invention having the general formula:

$$AlOH_{1.48}Cl_{3.0}SO_{4\ 0.10}Na_{1.68}\text{sulfosalicylic acid}_{0.04}.$$

EXAMPLE VI

The process of Example V is reproduced with the exception of the addition of sodium sulfate. Consequently, the product thus obtained is not within the scope of the present invention.

EXAMPLE VII

The process described in Example I is repeated with the exception that the citric acid is replaced by tartaric acid in a molecularly equal quantity. The product obtained is, accordingly, not within the scope of the present invention.

EXAMPLE VIII

An aluminum hydroxychloride composition is prepared as described in Example I except that the quantity of citric acid added is altered to yield, ultimately, 0.008 M/gram-atom of aluminum.

EXAMPLE IX

An aluminum hydroxychloride composition is prepared as described in Example I with the exception that the quantity of citric acid added is adjusted to yield, ultimately, 0.12 M/gram-atom of aluminum.

EXAMPLE X

The process described in Example I is reproduced except that the citric acid is replaced with pyrocatechol 3,5-disulfonic acid, added in the form of its disodium salt in a quantity of 0.03 M/gram-atom of aluminum.

EXAMPLE XI

The process described in Example I is reproduced with the exception that the citric acid component is replace with chromotropic acid in a quantity of 0.03 M/gram-atom of aluminum.

In order to demonstrate the superior ability of products produced in accordance with the present invention to purify water and to further demonstrate, by comparison, the results obtained from products not within the scope of the present invention, coagulation tests are conducted employing the conventional "jar-test" method. This method comprises treating synthetically charged water, obtained by adding powdered kaolin, at 100 mg/l., to water of various degrees of hardness expressed in degrees TH (French hydrotimetric value, 1°TH corresponding to 10 mg (Ca and Mg) expressed as Ca $CO_3$/l.), with a dose of each product obtained above, corresponding to 5 mg of $Al_2O_3$/l. of water. This mixture is agitated for 1 minute at 120 rpm, at which time the speed of agitation is reduced to 40 rpm and maintained at that value for 20 minutes. After the speed has been reduced to 40 rpm the time when floccules begin to appear is noted; agitation is stopped and the dimension of the floccules is also noted; and, the time for the floccules to be decanted is noted. The dimensions are recorded, being assessed on the following scale from 0 to 10:

0—no floccules
2—floccules hardly visible
4—small dots
6—floccules of average dimensions
8—coarse floccules
10—very coarse floccules The results obtained by treatment in accordance with this test are set forth in the following Table for various degrees of water hardness:

TABLE

| Example | Products | TH of water treated | Beginning of appearance of floccules in minutes | Dimensions of floccules | Decantation time in minutes |
|---|---|---|---|---|---|
| 1 | $SO_4$ $_{0.15}$ | 30 | 0.5 | 10 | 1 |
|   | Citric acid$_{0.04}$ | 3 | 2 | 8 | 2 |
|   |   | 1.5 | 4 | 8 | 3 |
| 2 | $SO_4$ $_{0.15}$ | 30 | 0.5 | 10 | 1 |
|   |   | 3 | 15 | 2 | 5 |
|   |   | 1.5 | 20 | 0 | 5 |
| 3 | Citric acid$_{0.04}$ | 30 | 3 | 4 | 3 |
|   |   | 3 | 15 | 4 | 5 |
| 4 | Citric acid$_{0.15}$ | 30 | 3 | 4 | 3 |
|   |   | 3 | 5 | 4 | 4 |
| 5 | $SO_4$ $_{0.10}$ | 30 | 1 | 10 | 1 |
|   | Sulfosalicylic acid$_{0.04}$ | 3 | 2 | 10 | 1.5 |
|   |   | 1.5 | 3 | 8 | 2 |
| 6 | Sulfosalicylic acid$_{0.04}$ | 30 | 3 | 6 | 3 |
|   |   | 3 | 10 | 4 | 5 |
| 7 | $SO_4$ $_{0.15}$ | 30 | 1 | 10 | 1 |
|   | Tartaric acid$_{0.04}$ | 3 | 15 | 2 | 5 |
| 8 | $SO_4$ $_{0.15}$ | 3 | 6 | 6 | 3 |
|   | Citric acid$_{0.008}$ | 1.5 | 13 | 4 | 5 |
| 9 | $SO_4$ $_{0.15}$ | 3 | 2 | 10 | 1.5 |
|   | Citric acid$_{0.12}$ | 1.5 | 3 | 8 | 2 |
| 10 | $SO_4$ $_{0.15}$ | 3 | 2 | 10 | 1.5 |
|    | Tiron$_{0.03}$ | 1.5 | 3 | 8 | 2 |
| 11 | $SO_4$ $_{0.15}$ | 3 | 2 | 10 | 1 |
|    | Chromotropic acid$_{0.03}$ | 1.5 | 3 | 8 | 2 |

Summarizing the data, the following comparisons may be made:

(1) Examples I, V, IX, X, and XI illustrate the beneficial results obtained upon addition of certain organic additives along with the $SO_4^{-2}$ anion whereby the efficacy of such compounds in the treatment of soft water parallels closely the excellent results commonly obtained in the treatment of hard water with similar products containing only the $SO_4^{-2}$ anion.

(2) Examples II, III, IV, and VI demonstrate that, although sulfate is the best exemplified additive, when employed alone for the treatment of hard water, its effect on treatment of soft water is virtually non-existent. Similarly, the action of citric and sulfosalicylic acids, when used alone, is weak and varies but little with the degree of hardness of the water.

(3) Examples I and VII show the importance of the nature of the organic anion added to the hydroxychloride compositions. Thus, tartaric acid which exhibits numerous chemical properties strikingly resembling those of citric acid, is virtually ineffective. Tartaric acid forms cationic complexes with aluminum, whereas citric acid, for example, forms non-charged and anionic complexes therewith, apparently accounting for the distinction.

(4) Examples I, VIII, and IX indicate that the quantity of organic anion added must be at least 0.01 M/gram-atom of aluminum if suitable results are to be obtained, but that there is no significant advantage in substantially increasing the quantity thereof.

(5) Examples I and V demonstrate the fact that the time of addition of the organic anion to the hydroxychloride is not a controlling consideration, such addition being accomplishable at any stage in the preparation of the compositions.

In capsule summary, therefore, the foregoing data dramatically indicate the superior results of the compounds based upon aluminum hydroxychlorides prepared in accordance with the present invention and employed in the treatment of soft water. The problem which have persisted in this area and which have been unsuccessfully resolved by prior art techniques and compounds are, thus, successfully overcome.

While the invention has now been described in terms of preferred embodiments, and exemplified and compared with conventional compositions, the skilled artisan will appreciate that various substitutions, omissions, modifications, and changes may be made without departing from the spirit thereof. Accordingly, it is intended that the scope of the invention be limited solely by the following claims.

What is claimed is:

1. A composition of matter comprising (i) aluminum hydroxychloride, (ii) $SO_4^{-2}$ anions in an amount of from about 0.05 to 0.3 M/gram-atom of aluminum present, and (iii) at least one anion of an organic acid selected from the group consisting of citric acid, sulfosalicyclic acid, pyrocatechol-3,5-disulfonic acid, chromotropic acid and mixtures thereof, said anion forming anionic or uncharged complexes with aluminum in a neutral or nonacidic medium and said anion being present in an amount of at least about 0.01 M/gram-atom of aluminum present, and (iv) said composition exhibiting a basicity, expressed as the ratio OH/Al, of from about 1.2:1 to 1.7:1.

2. The composition of matter as defined by claim 1, said organic acid being citric acid.

3. The composition of matter as defined by claim 1, said anion being present in an amount of up to about 0.1 M/gram-atom of aluminum present.

4. An aqueous solution of the composition of matter as defined by claim 1.

* * * * *